(12) United States Patent
Desponds et al.

(10) Patent No.: US 9,095,278 B2
(45) Date of Patent: Aug. 4, 2015

(54) METHOD FOR MONITORING A RADIATION DOSE

(75) Inventors: Lionel Desponds, St Remy-les-chevreuse (FR); Pál Tegzes, Budapest (HU); Székely György, Budapest (HU); Régis Vaillant, Villebon sur Yvette (FR); Tamás Ujvári, Biatorbágy (HU); Zsolt Szabó, Somlóvásárhely (HU); Vincent Bismuth, Paris (FR)

(73) Assignee: GENERAL ELECTRIC COMPANY, Schenectady, NY (US)

(*) Notice: Subject to any disclaimer, the term of this patent is extended or adjusted under 35 U.S.C. 154(b) by 133 days.

(21) Appl. No.: 13/991,112

(22) PCT Filed: Oct. 25, 2011

(86) PCT No.: PCT/US2011/057657
§ 371 (c)(1),
(2), (4) Date: May 31, 2013

(87) PCT Pub. No.: WO2012/074627
PCT Pub. Date: Jun. 7, 2012

(65) Prior Publication Data
US 2013/0243162 A1     Sep. 19, 2013

(30) Foreign Application Priority Data
Dec. 3, 2010 (FR) .................................. 10 60064

(51) Int. Cl.
*A61B 6/10* (2006.01)
*A61B 6/00* (2006.01)

(52) U.S. Cl.
CPC ............... *A61B 6/10* (2013.01); *A61B 6/4441* (2013.01); *A61B 6/488* (2013.01); *A61B 6/542* (2013.01); *A61B 6/547* (2013.01); *A61B 6/548* (2013.01)

(58) Field of Classification Search
CPC .......... H05G 1/265; H05G 1/46; H05G 1/54; H05G 1/26; H01N 5/32; A61B 6/10; A61B 6/4441; A61B 6/488; A61B 6/542; A61B 6/547; A61B 6/548
USPC ................................................ 378/62, 97, 98
See application file for complete search history.

(56) References Cited

U.S. PATENT DOCUMENTS

| 2008/0103834 A1 | 5/2008 | Reiner | |
| 2008/0154085 A1* | 6/2008 | Jervis et al. | 600/3 |

(Continued)

FOREIGN PATENT DOCUMENTS

| DE | 10 2008 014738 | 9/2009 |
| DE | 10 2008 047811 | 4/2010 |

(Continued)

OTHER PUBLICATIONS

PCT Search Report and Written Opinion from corresponding PCT Application No. PCT/US2011/057657, Dated Dec. 1, 2011.

(Continued)

*Primary Examiner* — Irakli Kiknadze
(74) *Attorney, Agent, or Firm* — GE Global Patent Operation; Marc A. Vivenzio

(57) ABSTRACT

A method for monitoring a radiation dose applied to a patient being exposed or having been exposed to radiation from a medical imaging system, the medical imaging system comprising an X-ray source, the X-ray source describing a trajectory in a coordinate system of reference of the medical imaging system having an origin, the method comprising determining the current coordinates, in the coordinate system of reference of the medical imaging system, of a current region being exposed or having been exposed to radiation from the X-ray source, of an envelope of a patient model, in relation to a current position of the X-ray source, determining, from the current coordinates, a current coordinate system of reference having as origin the current position of the X-ray source, the current coordinate system of reference being centered on the current region, and displaying a representation of the current region centered on the current coordinate system of reference.

17 Claims, 6 Drawing Sheets

(56) References Cited

U.S. PATENT DOCUMENTS

2009/0238329 A1  9/2009  Haras
2010/0020917 A1  1/2010  Gaglliano
2010/0290591 A1  11/2010  Spahn

FOREIGN PATENT DOCUMENTS

DE  10 2009 021239  11/2010
WO  2007080522  7/2007
WO  2008061565  5/2008

OTHER PUBLICATIONS

French Search Report from corresponding French Application No. 1060064, Dated Jul. 26, 2011.

K. Chugh, "A Computer-Graphic Display for Real-Time Operator Feedback during Interventional X-Ray Procedures", Proceedings of SPIE (2004) 5367:464-473.
E. Morrell, "Dosimetry and Optimisation in High Dose Fluoroscopic and Fluorographic Procedures", (Mar. 2006) Universiy of Nottingham, UK.
M. Ozeroglu, "Verification of Caregraph® Peak Skin Dose Data Using Radiochromic Film", pp. 1-49, Uniformed Services University of the Health Sciences, Bethesda MD, USA, Jun. 2005.
O. Rampado, "A method for a real time estimation of entrance skin dose distribution in interventional neuroradiology" Med. Phys. (2004) 31, 2356-2361.
A. Boer, "Real-time Quantification and Display of Skin Radiation During Coronary Angiography and Intervention", Circulation (2001) 104:1779-1784.

* cited by examiner

FIG. 3
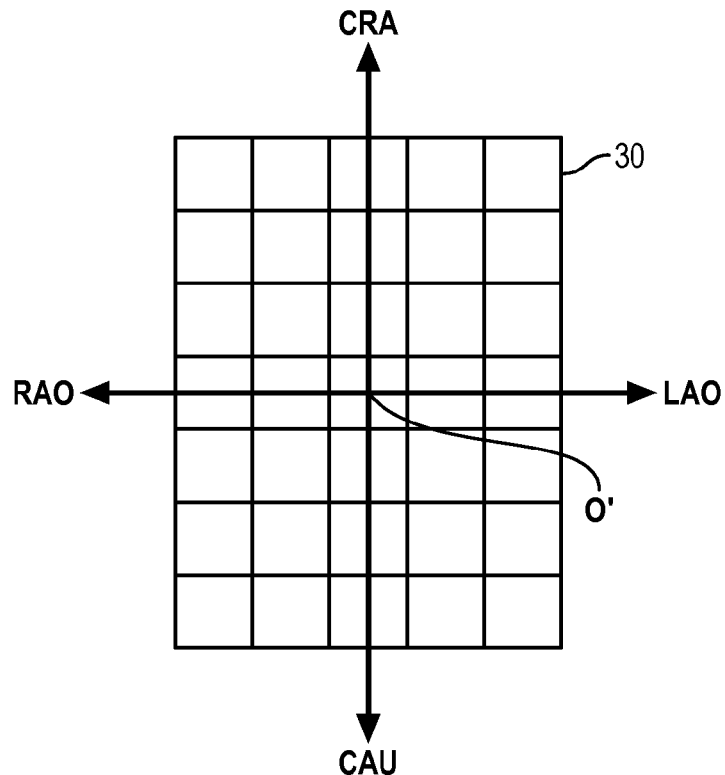
FIG. 5
FIG. 4A
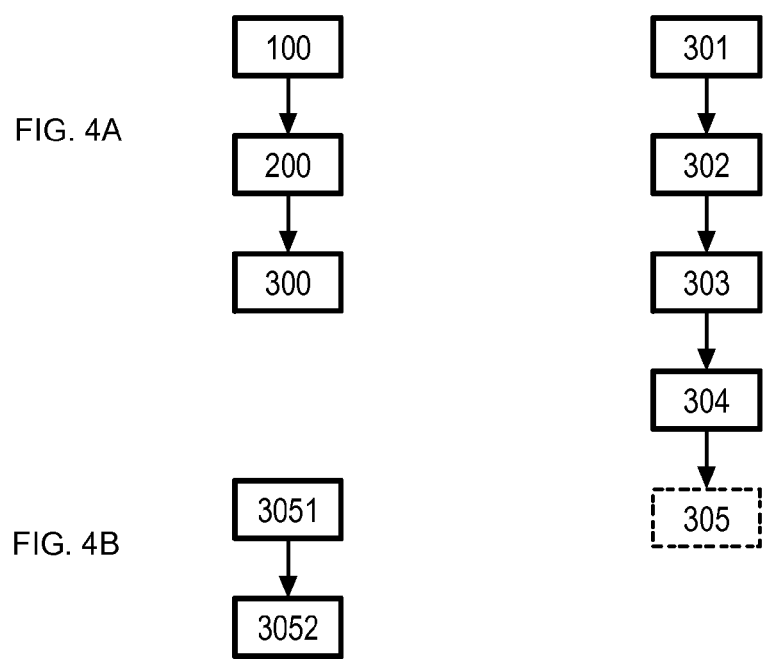
FIG. 4B

METHOD FOR MONITORING A RADIATION DOSE

CROSS REFERENCE TO RELATION APPLICATION

This is the national stage application under 35 U.S.C. §371 (c) of prior filed, co-pending PCT Application serial number PCT/US2011/057657, filed on Oct. 25, 2011, which claims priority to French Patent Application number 1060064, filed on Dec. 3, 2010, the disclosures of which are hereby incorporated in their entirety by reference herein.

FIELD OF THE INVENTION

Embodiments of the present invention relate to the field of medical imaging using radiation and more particularly, related to the estimation and monitoring of radiation doses to which a body or some organs thereof are subjected, when acquiring images by means of a radiation imaging system. Embodiments of the present invention also relate to the real-time monitoring of radiation doses to which a patient is subjected during radiological procedure.

BACKGROUND OF THE INVENTION

Exposure of a patient to X-rays produces two types of effects:—stochastic, long-term effects (cancer risk) are related to the dose accumulated by patients throughout their lifetime, from this perspective, any radiation dose must be weighed against the benefit for the patient, and short-term effects over the hours, days and weeks following after exposure (burns), these are related to short-time exposure at very high dose.

Yet, radiation imaging can expose a patient's body or some parts thereof to radiation doses which may vary substantially from one acquisition to another, particularly in relation to the chosen directions of exposure.

Also, radiation and notably X-rays interact very differently with the bones or tissues of the human body, preventing easy understanding of the level of radiation to which a given part of the body can still be exposed.

There is therefore a need for the monitoring of radiation doses received by a body or by different parts thereof during an examination involving one or more acquisitions of radiological images.

It is also desired, when acquiring new images, to avoid accumulating too excessive radiation doses in some body regions or in some organs, and hence to be able to determine the acquisition conditions for subsequent images allowing optimization of the radiation doses accumulated in a body.

Methods are known to estimate the distribution of radiation doses accumulated in a patient's body.

However, with these methods it is not possible to determine how the position of the X-ray source can be modified to prevent too strong exposure of a body region.

BRIEF SUMMARY OF THE INVENTION

An objective of the invention is to be able, at all times, to monitor the dose quantity of radiation a body region of a patient is exposed to, and optionally to be able to determine how to re-position the medical imaging system to irradiate a different region. According to a first aspect, the invention concerns a method for monitoring a radiation dose applied to a patient being exposed or who has been exposed to radiation by a medical imaging system, the medical imaging system comprising an X-ray source, the method comprising the following steps:—in relation to a current position of the X-ray source; determining a distribution of the dose on a current region of an envelope of a patient model, such distribution corresponding to the interaction between the radiation of the source at the current position and said current region; displaying a representation of the envelope of the patient model with the current region.

Other embodiments include: a step to determine the coordinates of the current region, within the current coordinate system of reference, the current region being defined by a closed surface delimited by at least three points, the step comprising determining a difference between the coordinates of the points in the coordinate system of reference of the medical imaging system and the coordinates of the current position of the X-ray source in the coordinate system of reference of the medical imaging system; the display of two-dimensional mapping of the model envelope, mapping comprising at least one region being exposed or having been exposed, the display being centered on the current region; a step to determine a position of the X-ray source in the coordinate system of reference of the imaging system, to expose a region determined from the map centered on the current coordinate system of reference; a step to associate a dose value with each region of the model envelope, the dose being defined by air kerma; the dose associated with each region corresponds to an accumulation of a plurality of dose values derived from previous exposure; a step to determine a three-dimensional model of the patient defined by an envelope, the model being chosen from among the following group: cylinder, sphere, flat cylinder; and the display of the representation of the current region is superimposed over a radiological image of the patient.

According to an embodiment, there is provided a method for monitoring a radiation dose applied to a patient being exposed or having been exposed to radiation by a medical imaging system, the medical imaging system comprising an X-ray source. The method comprising the following steps: in relation to a current position of the radiation source, determining a distribution of the dose on a current region of an envelope of a patient model, said distribution corresponding to the interaction between the radiation of the source at the current position and said current region; displaying a representation of the envelope of the patient model with the current region.

An embodiment of the method further comprises: for a region of the patient model, the determining of the interaction and distribution of the accumulated dose depends on one or more parameters: air kerma which depends on exposure and the X-ray beam, the quantity of dose absorbed by the patient's skin, the backscattering coefficient, the coefficient of dose entry into the patient; for a region of the patient model, the determining of the interaction and distribution of the accumulated dose also depends on the following parameters of the medical imaging system, such as the geometric characteristics of emission the properties of the emission tube, and the emitted focal spot size; and a step to determine the current region being exposed or having been exposed to the X-ray source at the current position. In an embodiment, the representation of the patient model is two-dimensional or three-dimensional. In an embodiment, the display comprises centering the patient model on the current region in relation to the current position of the X-ray source.

According to an embodiment, there is provided a medical imaging system comprising a processing unit to implement a method applied to a patient being exposed or who has been exposed to radiation by a medical imagining system.

According an embodiment, there is provided a computer program comprising machine instructions to implement a method applied to a patient being exposed or who has been exposed to radiation by a medical imaging system.

The present invention has the advantage of at least allowing the monitoring of exposed regions in relation to the position of the X-ray source of the medical imaging system.

It is through the use of angle coordinates in two-dimensional form that the monitoring of exposed regions, notably in terms of emitted dose, can be facilitated.

With each new position of the X-ray source, a practitioner can determine which region is exposed and can determine possible re-positioning to be applied to the source to expose a region of interest.

BRIEF DESCRIPTION OF THE DRAWINGS

Other characteristics and advantages of the present invention will become further apparent from the following description which is solely illustrative and non-limiting, and is to be read in connection with the appended drawings in which:

FIG. 3 illustrates a 2D map of a patient model according to an embodiment of the present invention;

FIGS. 4A, 4B, and 5 schematically illustrate method according to an embodiment of the present invention;

DETAILED DESCRIPTION OF THE INVENTION

Medical Imaging System

Figure 1:
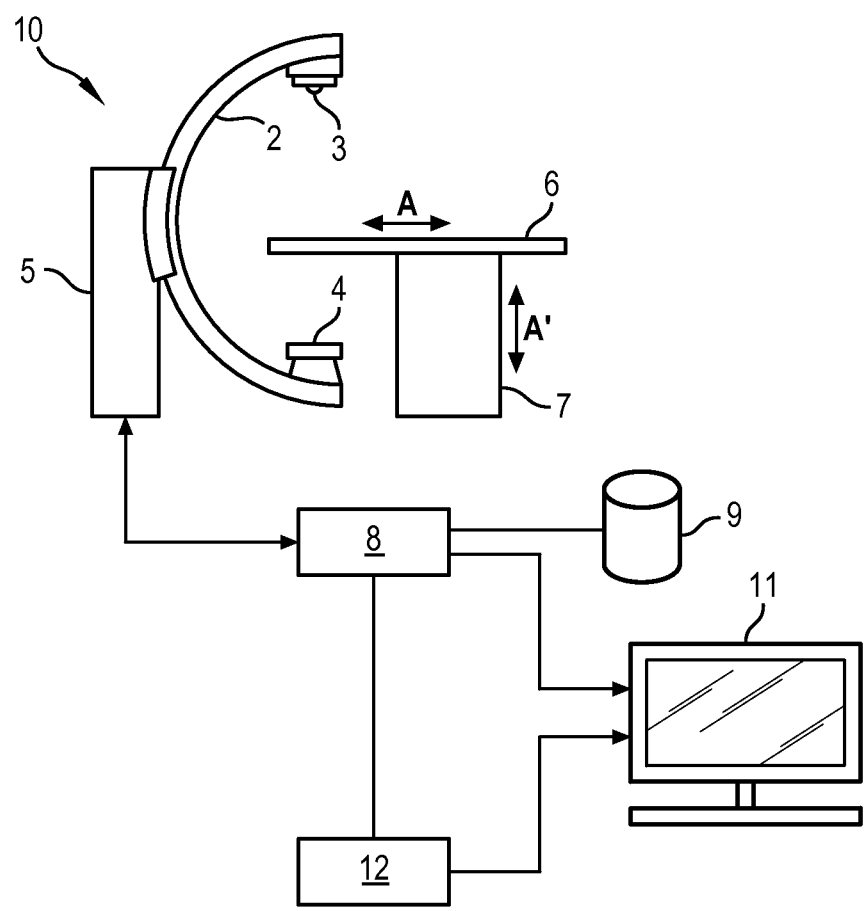
FIG. 1 illustrates a medical imaging system conforming to an embodiment the present invention.

FIG. 1 illustrates a medical imaging device 10 with a C-arm used for examining a patient. This X-ray medical imaging device 1 comprises a C-arm 2 on which an X-ray source 3 and a detector 4 are arranged facing one another. The C-arm 2 is mounted on a stand 5. The C-arm 2 can be moved in different directions D, D', relative to stand 5.

Figure 2:
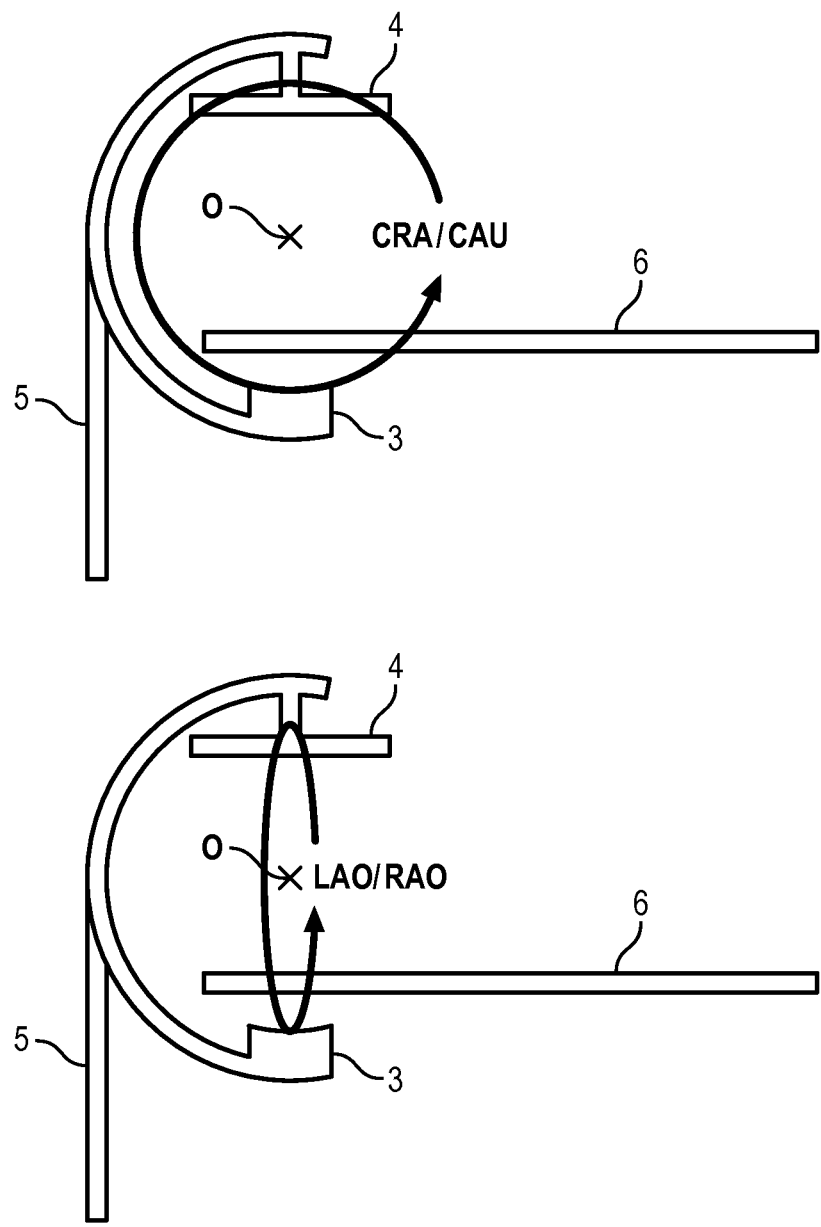
FIG. 2 schematically illustrates the conventions used to locate elements within a coordinate system of reference of a medical imaging system of origin according to an embodiment of the present invention.

In manner known per se, the movements of the X-ray source are referenced in a coordinate system of reference of the medical imaging system defined by a Cranio-Caudal axis (CRA/CAU) and by a Right Anterior Oblique/Left Anterior Oblique axis (RAO/LAO) which are perpendicular to each other and intersect at an iso-centre (O) in an isocentric system. FIG. 2 illustrates said conventions.

The medical imaging device 1 may comprise a table 6 intended to receive an object to be imaged e.g. a patient. The table 6 in this case is arranged on a base 7 and can be moved in several directions A, A' relative to the base 7.

The detector 4 may be a semiconductor image sensor comprising caesium iodide phosphor (scintillator) for example on a transistor/photodiode array in amorphous silicon. Other suitable detectors are: a CCD sensor, direct digital detector which directly converts X-rays into digital signals, or a detector with image enhancer. The detector 4 illustrated in FIG. 1 is planar and defines a planar image surface, however other geometries are possible.

The device comprises a control unit 6 connected to the C-arm 2 via wire or wireless connection. The control unit 6 is used to control acquisition by setting parameters such as radiation dose to be emitted by the X-ray source and angle position of the C-arm 2. The control unit 6 can also be used to control the positioning of the C-arm 2.

The control unit 6 may comprise a reader device (not illustrated) e.g. a diskette reader, CD-ROM, DVD-ROM reader or connection ports to read the instructions for a control or processing method from an instruction medium (not illustrated) such as a diskette, CD-ROM, DVD-ROM or USB key or in general using any removable storage medium or via a network connection.

In an embodiment, a storage unit 9 is connected to the control unit 8 to record image parameters acquired during a radiological examination for example. It is possible to make provision so that the storage unit 9 is located inside or outside the control unit 8.

The storage unit 9 can be formed of a hard disk or SSD, or any other removable, re-write storage means (USB keys, memory cards, etc.). The storage unit 9 may be a ROM/RAM memory of the control unit 8, USB key, memory card, memory of a central server.

Also, in an embodiment, the display unit 11 is connected to the control unit 8 to display mapping of a patient model as part of a method for monitoring a radiation dose applied to a patient being exposed or having been exposed to radiation by the medical imaging system. The display unit 11 for example may be a computer screen, a monitor, flat screen, plasma screen or any other type of display device of known type. Said display unit 11 may be the same as the one used to display radiological images derived from acquisition by means of the medical imaging system. In an embodiment, to perform processing on the acquired images, the medical imaging device also comprises a computing unit 12.

Transmission of data from the storage unit 9 to the computing unit 12 can be made via an internal or external computer network or by means of any suitable physical memory medium such as CD-ROM, DVD-ROM, external hard disk, USB key, SD card, etc. In an embodiment, the computing unit 12 is one or more computers, or one or more processors, one or more microcontrollers, one or more microcomputers, one or more programmable logic controllers, one or more application-specific integrated circuits, other programmable circuits, or other devices which include a computer such as a workstation.

As a variant, the computing unit 12 may comprise a reader device (not illustrated) for example a diskette reader, CD-ROM or DVD-ROM reader, or connection ports to read the instructions of the processing method from an instruction medium (not illustrated) e.g. a diskette, CD-ROM, DVD-ROM, or USB key or more generally any removable memory medium or via a network connection.

The computing unit 12 may be connected to the display unit 11 (as in FIG. 1) or to another display unit (not illustrated).

Method for monitoring a radiation dose applied to a patient being exposed or having been exposed to radiation of a medical imaging system.

In an embodiment, to monitor a dose (effective dose, absorbed dose) of radiation applied to a patient being exposed or having been exposed to radiation of the medical imaging system, a first step 100 determines a three-dimensional (3D)

patient model for which, at a second step 200, one or more dose values are determined, these dose values being associated with regions of the patient model.

Finally, to allow the practitioner to visualize the determined doses associated with the different regions of the patient model, at a third step 300 a representation of the patient model is displayed. This display may or may not be centered on a current region corresponding to a current position of the X-ray source.

Determination 100 of the Patient Model

In an embodiment, the patient model is a three-dimensional (3D) model which may depend on physiological parameters of the patient (weight, height, gender, etc.) and on several parameters of the medical imaging system. The physiological parameters are derived for example from an examination carried out prior to a radiological examination.

The 3D model can be approximated by a cylindrical shape enveloping the patient. More complex shapes can be envisaged: spherical, flat cylinder. The shape of the 3D model can be optimized by acquisition of patient contours or using conventional segmenting and reconstructing techniques from a plurality of acquired 2D images of the patient. In an embodiment, the 3D model may also depend on variations in density of the different constituent parts of the patient.

In an embodiment, the 3D model of the patient is stored in a storage unit 9 of the medical imaging system in the form of an envelope of the model that assumes the shape of a mesh, each region of the mesh being defined by a plurality of vertices. The vertices correspond to the X-ray emission field for a current position of the X-ray source.

This mesh corresponds to sampling of the envelope of the 3D patient model in relation to the position of the X-ray source.

FIG. 3 illustrates a mesh 30 corresponding to an envelope of a cylindrical 3D model of the patient in which the axes CRA/CAU and RAO/LAO are shown corresponding to a patient lying down, the centre O here being the isocentre of an isocentric medical imaging system.

To obtain a more precise patient model, the model may also depend on Equivalent Patient Thickness EPT of the patient's body. This is an estimate of the thickness of the patient's body through which the X-rays are to pass. This thickness provides data on X-ray requirements in order to be able to take an image of a given region of the patient's body. It will be understood that the greater the thickness, the more the X-ray emission dose must be increased.

In an embodiment, to improve the precision of the patient model, the following parameters can be taken into account: emission characteristics (voltage in kV, intensity in mA); and properties of the emission tube; and emitted focal spot size.

In an embodiment, the 3D model can be determined at the start of procedure and updated during the procedure. To update the 3D model, the images acquired during the radiological examination are used.

Determination 200 of one or more dose values associated with one or more regions of the patient model.

In an embodiment, the determination 200 of dose values for each region of the patient model depends upon one or more parameters from among: air kerma, dependent upon exposure and the X-ray beam; the quantity of dose absorbed by the skin; the backscattering coefficient which may be seen as an X-ray filtering effect; and the coefficient of dose entry into the patient.

In an embodiment, for each dose value, in addition to the above-mentioned parameters, it is necessary to take into account the geometry associated with each exposure namely the following parameters of the medical imaging system: the emission characteristics (voltage in kV, intensity in mA); the properties of the emission tube; and the emitted focal spot size.

For precision of dose calculation, with each acquired image, the dose distribution is to be measured and the patient model modified. However, throughout an examination up to $10^5$ images may be acquired which gives rise to a problem of storage for all this data, and the needs in terms of computing power are considerable.

An embodiment of the present invention solves said problem by computing the above-discussed parameters for each image, and by accumulating these with dose measurements which correspond to images already acquired using the same acquisition geometry. With said approach, the necessary storage capacity and computing power are reduced.

Display 300 of a Representation of the Patient Model

In an embodiment, the display 300 of a representation of the patient model comprises displaying the dose distribution on the envelope of the patient model.

The purpose is to associate several regions of the patient model with a dose value. Said representation of dose distribution on the envelope of the patient model comprises the succession of following steps: determination 301 of vertices A, B, C, D delimiting a region Z exposed by the X-ray source; determination 302 of the centre $C_1$, $C_2$, $C_3$, $C_4$ of each ray $R_1$, $R_2$, $R_3$, $R_4$ emitted by the X-ray source 3 towards each vertex A, B, C, D; determination 303 of the angle $\alpha_1$, $\alpha_2$, $\alpha_3$, $\alpha_4$ between a ray travelling from the X-ray source 3 towards a vertex, and the normal to this apex; associating 304 with each region a previously defined dose value; and optional centering 305 of the display on a current region or region of interest.

In other words, for each position of the X-ray source, a region of the patient model exposed by the source at this position is determined and the dose value measured for this position is associated therewith.

FIG. 4 illustrates a region 2 delimited by four vertices A, B, C, D, corresponding to a field emitted by the X-ray source. The display can take into account the type of backscattering which is considered to be a filter which is applied to each region of the patient envelope.

Finally, the representation can be made in several manners: 3D display of the complete patient model with: rendering of 3D surfaces by solid surfaces, and colour scale representing the dose quantity; rendering of 3D surfaces by semi-transparent surfaces, and a colour scale representing dose quantity inside/outside the surfaces of the model. In this manner, a practitioner is provided with data outside and inside the model; rendering of 3D surfaces by semi-transparent surfaces of a realistic patient model (concave surfaces allowed) positioned inside; or combination of any of the above representations. The representation can also be made in 2D display of the patient model: Display of the developed envelope (see FIG. 3), the abscissa axis being indexed in terms of angles taken along axes RAO/LAO and CRA/CAU with a colour scale representing dose quantity.

In an embodiment, the mapping display can be merged with or superimposed over an acquired radiological image to identify structures in the imaged region which must not be irradiated. In another embodiment, the image viewpoint may be the X-ray emission focal spot instead of the centre of a reference point in the medical imaging system.

Centering of the Display 305

In an embodiment, the display of a representation of the envelope of the patient's 3D model such that the representation is centered on a current region or region of interest.

This so-called current region is either a region in the process of being exposed to the X-ray source or a region which has already been exposed: it is therefore a region of interest.

The purpose therefore is to allow a practitioner to visualize the current region that is of interest, and in addition to determine how to control the movement of the X-ray source from this current region.

Figure 7A:
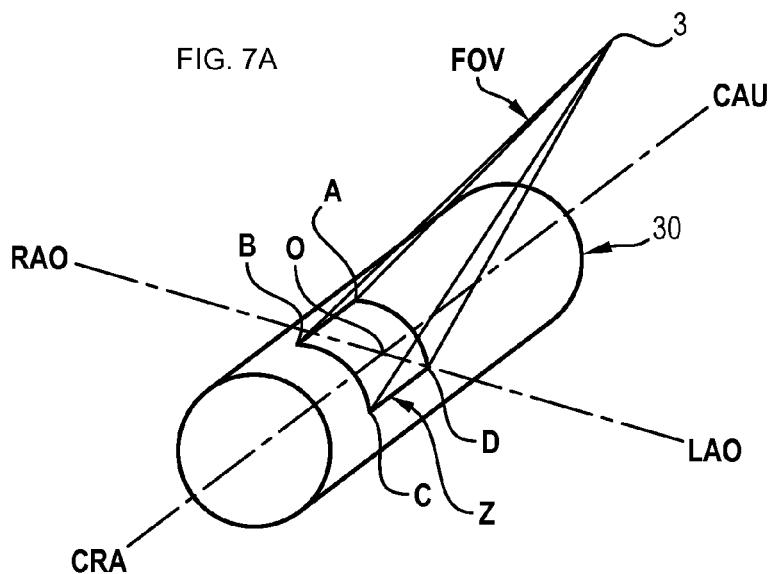
FIGS. 7A, 7B, and 7C illustrate the locating of an exposed region within the coordinate system of reference of the medical imaging system and within a current coordinate system of reference according to an embodiment of the present invention.

FIG. 7A illustrates a cylindrical 3D model of the patient, showing a region Z exposed to the X-ray source 3 and a reference point of the medical imaging system defined by an origin O and two axes perpendicular to each other: the craniocaudal axis (CRA/CAU), the left anterior oblique/right anterior oblique axis (LAO/RAO). These two axes intersect at the origin O of the reference point thus defined.

It is specified here that the reference point may be any reference point. For example, in an isocentric system, the origin may be the isocentre of the medical imaging system. These axes correspond to a patient lying down in the field of the medical imaging system.

The exposed region Z is a function of the Field of View (FOV) of the X-ray source 3. Again with reference to FIG. 3, the region Z is defined here by four vertices A, B, C, D taken on the outer envelope of the 3D patient model. The region Z is a closed surface, preferably convex, defined by these four vertices. As already mentioned, the envelope of the 3D model may be broken down into several regions, each region corresponding to an angle position of the X-ray source. The four vertices A, B, C, D are identified by their angle coordinates in the coordinate system of reference of the medical imaging system of origin O. Each point is defined by two angle coordinates; one on the CRA/CAU axis the other on the LAO/RAO axis.

These angle coordinates are respectively the polar coordinate of the projection of each point defining the region Z in the planes containing the CRA/CAU axis and the LAO/RAO axis. The term "angle coordinates" is used when locating a region in the coordinate system of reference of the medical imaging system. The region Z depends on the position of the X-ray source which itself may be defined by angle coordinates in the same manner as the vertices A, B, C, D defining the region Z.

So that use can be made of the position of the exposed region Z, notably during radiological procedure, the angle coordinates of the four vertices delimiting the region Z are projected in a current coordinate system of reference of origin O' centered on the current region Z (i.e. the region being exposed or the region for which an acquisition has been made). The current coordinate system of reference here is a 2D reference.

Figure 7B:
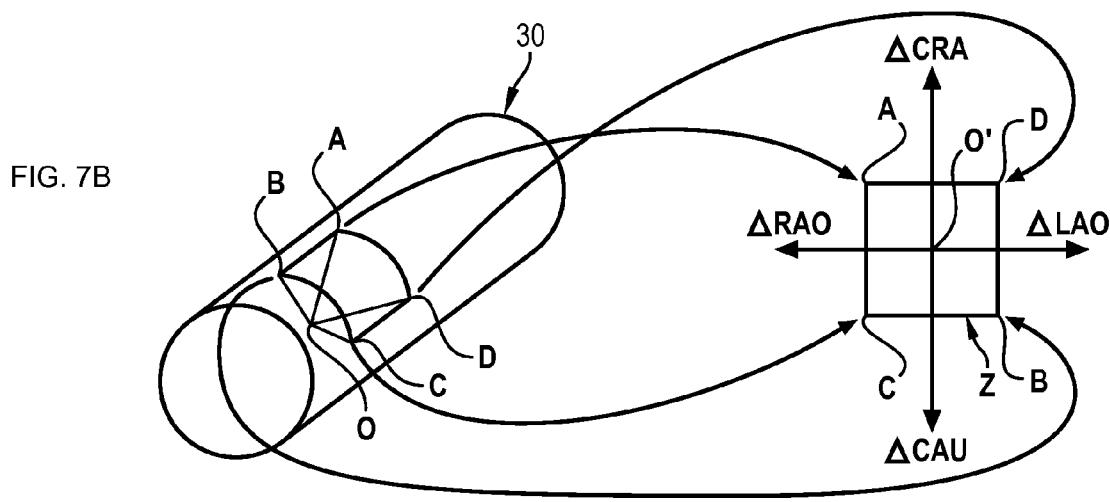

FIG. 7B illustrates the projection of the angle coordinates of the exposed region in the current coordinate system of reference of origin O'. The term projection is meant a representation of the angle coordinates in a 2D reference, with abscissa corresponding to the angle taken along the LAO/RAO axis and ordinate corresponding to the angle taken on the CRA/CAU axis. This convention is in no way limiting.

The coordinates of the four vertices A, B, C, D in the current coordinate system of reference are relative coordinates since they depend on the current position of the X-ray source 3.

In an embodiment, to obtain the coordinates in the current coordinate system of reference, the angle coordinates of the region in the coordinate system of reference of the medical imaging system are determined and then recalculated relative to a current coordinate system of reference of origin O' corresponding to the current position of the X-ray source.

This entails subtracting the current angle coordinates of the X-ray source (those taken in the coordinate system of reference of the medical imaging system) from the current coordinates of each point defining the current region Z i.e. the region in the current field of the X-ray source.

Figure 7C:
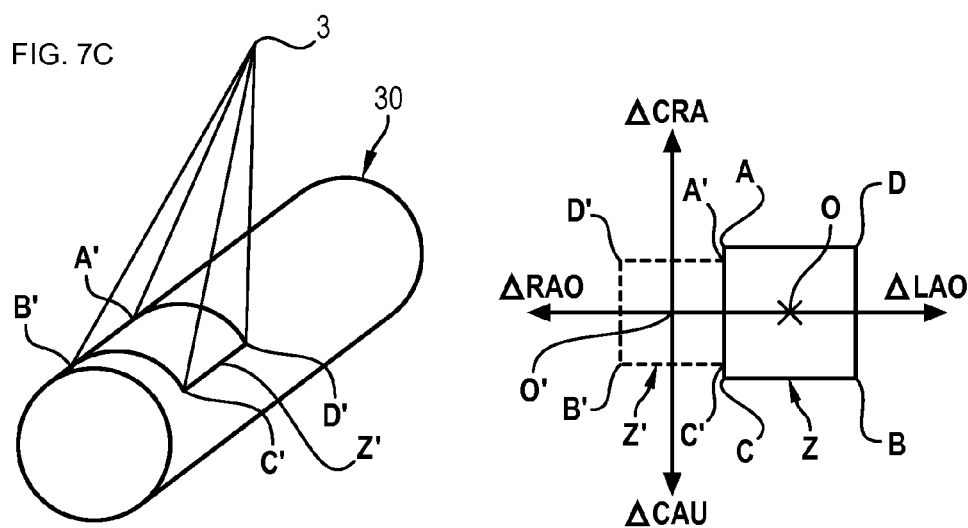

FIG. 7C illustrates the projection of the angle coordinates of a region Z' adjacent to the region in FIG. 7B. This other region Z' has vertices A', B', C' and D'.

Figure 8:
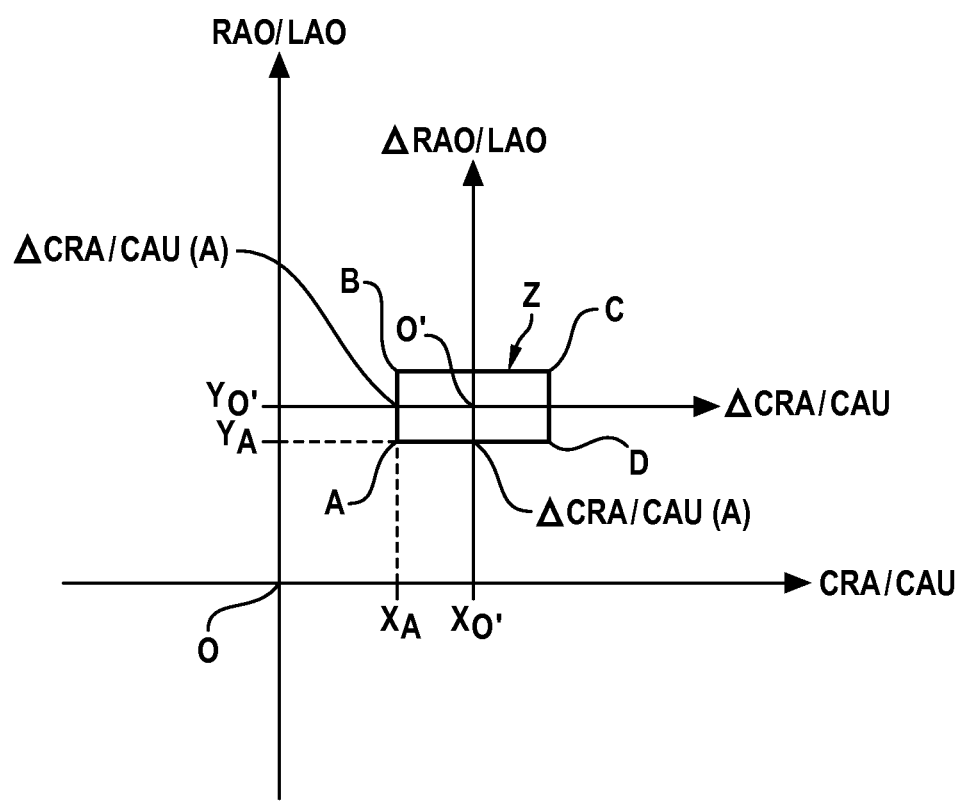
FIG. 8 schematically illustrates centering of the envelope of a patient model on a current region, according to an embodiment of the present invention.

FIG. 8 schematically illustrates the changeover from the coordinate system of reference of the medical imaging system of origin O to the current coordinate system of reference of origin O'.

Again with reference to FIG. 8, the coordinates of vertex A in the coordinate system of reference of the medical imaging system are XA and Ya, and the coordinates of vertex A in the current coordinate system of reference with origin O' are given by $\Delta_{RAO/LAO} = X_A - X_{O'}, \Delta_{CRA/CAU} = Y_A - Y_{O'}$, where $X_{O'}$, $Y_{O'}$ are the coordinates of the X-ray source projected in the coordinate system of reference of the medical imaging system which correspond to the region Z exposed by this position of the X-ray source.

The projection of the angle coordinates in the current coordinate system of reference of origin O' allows the display of a 2D representation of the exposed region centered on the current coordinate system of reference.

For a current position of the X-ray source, this allows the determination of which current region is being exposed.

In an embodiment, the display of the 2D mapping of the envelope of the patient model can be centered on the current coordinate system of reference.

Figure 6:
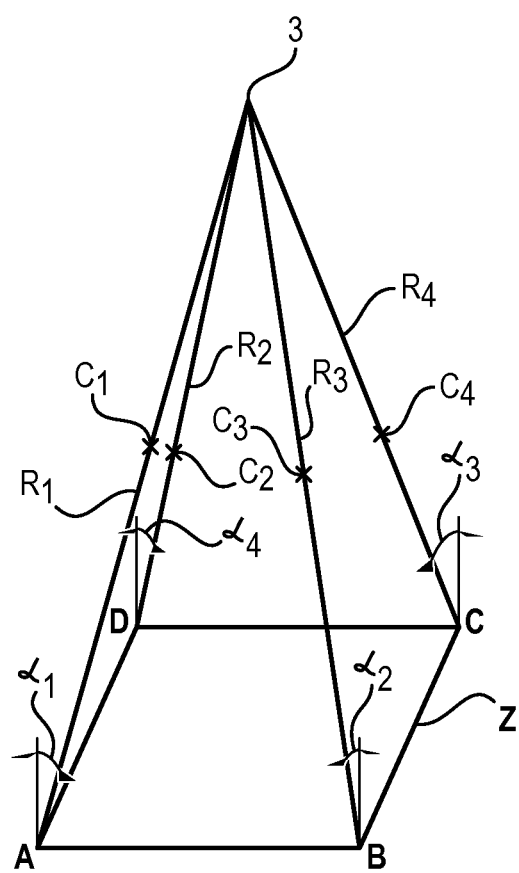
FIG. 6 schematically illustrates the determining of a region in an envelope of a patient model according to an embodiment of the present invention.

2D mapping, for a cylindrical 3D patient model, is in rectangular form as illustrated in FIG. 6, broken down into several regions.

A dose value can be associated with each region, such as described previously. A colour or grey scale can be used to represent the different dose values, a dark colour possibly indicating that there is a risk that the region may be highly exposed or was previously highly exposed.

The display of said mapping can be used in several manners. In an embodiment, the display can be used, for example, after exposure of the patient, to verify that this exposure has been safely conducted for the patient, certain regions not being excessively exposed.

The display can also be used to determine the best directions of exposure to be used for subsequent exposures, so as not to expose some regions of the patient to an excessive radiation dose.

The dose values can be updated on each re-positioning of the X-ray source. The dose distribution for each region being exposed or having been exposed is then optionally recomputed.

Computer Program

The method described in the foregoing can, in an embodiment, be implemented in the form of a computer programme comprising machine instructions to perform the steps of the method.

This written description uses examples to disclose the invention including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements with insubstantial difference from the literal language of the claims.

The invention claimed is:

1. A method for monitoring a radiation dose applied to a patient being exposed or having been exposed to radiation of a medical imaging system, the medical imaging system comprising an X-ray source, the X-ray source describing a trajectory in a coordinate system of reference of the medical imaging system having a first origin, the method comprising:
   determining angle coordinates of a current region in the coordinate system of reference of the medical imaging system having the first origin, wherein the current region comprises a region of an envelope of a patient model currently exposed or having been exposed to radiation of the X-ray source in relation to a current position of the X-ray source;
   determining angle coordinates of the current position of the X-ray source in the coordinate system of reference of the medical imaging system having the first origin;
   determining a difference between the angle coordinates of the current region and the angle coordinates of the current position of the X-ray source in the coordinate system of reference of the medical imaging system having the first origin;
   determining angle coordinates of the current region in a current coordinate system of reference having a second origin corresponding to the current position of X-ray source;
   projecting the angle coordinates of the current region in the current coordinate system of reference having the second origin; and
   displaying a representation of the current region centered on the current coordinate system of reference.

2. The method according to claim 1, further comprising:
   determining the angle coordinates of the current region in the current coordinate system of reference, the current region being defined by a closed surface delimited by at least three points; and
   determining a difference between the angle coordinates of the at least three points in the coordinate system of reference of the medical imaging system and the angle coordinates of the current position of the X-ray source in the coordinate system of reference of the medical imaging system.

3. The method according to claim 1, further comprising:
   displaying a display of a two-dimensional mapping of the envelope of the patient model, the two-dimensional mapping comprising at least one region being exposed or having been exposed, the display being centered on the current region.

4. The method according to claim 3, further comprising:
   determining a position of the X-ray source in the coordinate system of reference of the medical imaging system to determine the current region being exposed or having been exposed from the two-dimensional mapping centered on the current coordinate system of reference.

5. The method according to claim 1, further comprising:
   associating a dose value with each region of the envelope of the patient model, the dose value being defined by air kerma.

6. The method according to claim 5, wherein the dose value associated with each region corresponds to an accumulation of a plurality of dose values derived from prior exposure.

7. The method according to claim 1, further comprising:
   determining a three-dimensional model of the patient defined by an envelope, wherein the three-dimensional model is a cylinder, a sphere, or a flat cylinder.

8. The method according to claim 1, further comprising:
   superimposing the representation of the current region over a radiological image of the patient.

9. A medical imaging system comprising:
   a processing unit configured to:
   determine angle coordinates of a current region in a coordinate system of reference of the medical imaging system having a first origin, wherein the current region comprises a region of an envelope of a patient model currently exposed or having been exposed to radiation of the X-ray source in relation to a current position of the X-ray source;
   determining angle coordinates of the current position of the X-ray source in the coordinate system of reference of the medical imaging system having the first origin;
   determining a difference between the angle coordinates of the current region and the angle coordinates of the current position of the X-ray source in the coordinate system of reference of the medical imaging system having the first origin;
   determining angle coordinates of the current region in a current coordinate system of reference having a second origin corresponding to the current position of X-ray source;
   projecting the angle coordinates of the current region in the current coordinate system of reference having the second origin; and
   display a representation of the current region centered on the current coordinate system of reference.

10. The medical imaging system according to claim 9, wherein the processing unit is further configured to:
    determine the angle coordinates of the current region in the current coordinate system of reference, the current region being defined by a closed surface delimited by at least three points; and
    determine a difference between the angle coordinates of the at least three points in the coordinate system of reference of the medical imaging system and the angle coordinates of the current position of the X-ray source in the coordinate system of reference of the medical imaging system.

11. The medical imaging system according to claim 9, further comprising a display configured to display a two-dimensional mapping of the envelope of the patient model, wherein the two-dimensional mapping comprises at least one region being exposed or having been exposed, wherein the display is centered on the current region.

12. The medical imaging system according to claim 11, wherein the processing unit is further configured to determine a position of the X-ray source in the coordinate system of reference of the medical imaging system to determine the current region being exposed or having been exposed from the two-dimensional mapping centered on the current coordinate system of reference.

13. The medical imaging system according to claim 9, wherein the processing unit is further configured to associate a dose value with each region of the envelope of the patient model, wherein the dose value is defined by air kerma.

14. The medical imaging system according to claim 13, wherein the dose value associated with each region corresponds to an accumulation of a plurality of dose values derived from prior exposure.

15. The medical imaging system according to claim 9, wherein the processing unit is further configured to determine a three-dimensional model of the patient defined by an envelope, wherein the three-dimensional model is a cylinder, a sphere, or a flat cylinder.

16. The medical imaging system according to claim 9, wherein the processing unit is further configured to superimpose the representation of the current region over a radiological image of the patient.

17. A non-transitory, computer-readable medium storing program code instructions executable by a computer processor to perform a method for monitoring a radiation dose applied to a patient being exposed or having been exposed to radiation of a medical imaging system, the medical imaging system comprising an X-ray source, the X-ray source describing a trajectory in a coordinate system of reference of the medical imaging system having a first origin, the method comprising:

determining angle coordinates of a current region in the coordinate system of reference of the medical imaging system having a first origin, wherein the current comprises a region of an envelope of a patient model currently exposed or having been exposed to radiation of the X-ray source in relation to a current position of the X-ray source;

determining angle coordinates of the current position of the X-ray source in the coordinate system of reference of the medical imaging system having the first origin;

determining a difference between the angle coordinates of the current region and the angle coordinates of the current position of the X-ray source in the coordinate system of reference of the medical imaging system having the first origin;

determining angle coordinates of the current region in a current coordinate system of reference having a second origin corresponding to the current position of X-ray source;

projecting the angle coordinates of the current region in the current coordinate system of reference having the second origin; and displaying a representation of the current region centered on the current coordinate system of reference.

* * * * *